United States Patent [19]

Hamacher et al.

[11] Patent Number: 5,770,030
[45] Date of Patent: Jun. 23, 1998

[54] PROCESS FOR THE SEPARATION OF CARRIER-FREE RADIO-NUCLIDES FROM TARGET LIQUIDS, THE USE OF THE PROCESS AND AN ARRANGEMENT SUITABLE THEREFOR

[75] Inventors: Kurt Hamacher; Gerrit Blessing, both of Aachen, Germany

[73] Assignee: Forschungszentrum Jolich GmbH, Julich, Germany

[21] Appl. No.: 676,135
[22] PCT Filed: Jan. 10, 1995
[86] PCT No.: PCT/DE95/00025
  § 371 Date: Jul. 9, 1996
  § 102(e) Date: Jul. 9, 1996
[87] PCT Pub. No.: WO95/18668
  PCT Pub. Date: Jul. 13, 1995

[30] Foreign Application Priority Data

Jan. 11, 1994 [DE] Germany ................. 44 00 539.3

[51] Int. Cl.⁶ ................. B01D 59/40; G21G 1/10
[52] U.S. Cl. ................. 205/43; 205/688; 205/702; 205/755; 205/760
[58] Field of Search ................. 205/688, 43, 702, 205/755, 760; 204/272, 274, 277, 551

[56] References Cited

U.S. PATENT DOCUMENTS

| | | | |
|---|---|---|---|
| 4,400,250 | 8/1983 | Fairhurst | 204/551 |
| 5,425,858 | 6/1995 | Farmer | 204/551 |
| 5,454,924 | 10/1995 | Jansen et al. | 204/272 |

OTHER PUBLICATIONS

Recovery of [$^{18}$F]Fluoride from [$^{18}$O]Water in an Electrochemical Cell, by A. Lexoff et al., Appl. Radiat. Isot. vol. 40, No. 1 pp. 1–6, 1989.

*Primary Examiner*—Arun S. Phasge
*Attorney, Agent, or Firm*—Herbert Dubno

[57] ABSTRACT

Ionizable or polarizable, carrier-free radionuclides may be separated by electrofixation, from a low electric conductivity liquid target material in a flow cell fitted with a permanent electrode arrangement. The target liquid is separated while the fixing voltage is maintained; then the fixed radionuclide is removed again from the electrode, if required by heating, after switching off or reversing the poles of the field, after an optional intermediate rinsing.

11 Claims, 4 Drawing Sheets

5,770,030

PROCESS FOR THE SEPARATION OF CARRIER-FREE RADIO-NUCLIDES FROM TARGET LIQUIDS, THE USE OF THE PROCESS AND AN ARRANGEMENT SUITABLE THEREFOR

FIELD OF THE INVENTION

This application is a 371 of PCT/DE95/00025 filed Jan. 10, 1995.

The invention relates to a process for the separation of carrier radio-free nuclides from liquid or liquefiable target materials of low electrical conductivity which, by means of a nuclear process, especially by cyclotron irradiation, are produced in ionizable or polarizable form, and within an electrode arrangement can be recovered by applying an electrical field for electrofixing the nuclide on one of the electrodes and from which the nuclide can be recovered after removal of the target liquid by supplying a solvent for further processing with a shut-off field or a field of opposite polarity by dissolution. The invention further relate to the use of this process and a flow cell suitable therefor.

BACKGROUND OF THE INVENTION

In the production of radiotracer compounds which play a significant role in medicinal diagnostics, especially short-lived radionuclides are used which should be provided as much as possible in carrier-free form.

As a result, there is a need to provide a process which is as time-conserving as is possible with the highest possible marker yield in spite of the carrier-free operation and which additionally because of the use of expensive target materials, should allow recovery as free from losses as is possible.

An especially elegant process for the recovery of radio-nuclides for radiotracer technology utilizes cyclotron irradiation of target material for which as an illustrative example the generation of $^{18}F$ from $^{18}O$—$H_2O$ can serve: $^{18}F$ has a half life of about 110 minutes and is used, among other things, in the synthesis of $^{18}F$ fluorodesoxyglucose for positron emission tomography. It is produced by cyclotron irradiation from $^{18}O$—$H_2O$ which has a price contribution of about 150 German marks per gram to the process cost.

For about 8 years, the $^{18}F$ fluoride formed in the cyclotron from $^{18}O$—$H_2O$ has been separated by ion exchange whereby an $^{18}O$—$H_2O$ loss as well as a contamination thereof by organic contents of the ion exchanger and $^{16}O$—$H_2O$ admixtures by adherent moisture can arise.

There is also a procedure known wherein the target liquid, by the addition of basic phase transfer catalysts and/or carbonates, and $^{18}F$ fluoride can be separated by distillation.

The aforedescribed processes have been found to be clearly unsatisfactory notwithstanding the fact that they have been in use for extended periods.

The process of the type described at the inception of the application has already been investigated by D. Alexoff et al (Appl. Radiat. Isot. Vol. 40, No. 1, pages 1–6, 1989) which describes an electrochemical cell with crucibles which fit one within the other and from which the inner platinum crucible, serving as a cathode, can be adjusted in height by means of a micrometer screw and the outer crucible, comprised of graphite or a vitreous carbon, is provided in a decomposable PVC holder and is arranged via a kind of jack for liquid exchange.

The direct current source is controllable between 0 to 20 volts with current amplitudes of up to 1 ampere. As far as possible, field strengths of 100 to 300 V/cm are used.

For the use of graphite crucibles, $^{18}F$ yields of up to 70% are obtained. As a whole, cells with platinum electrodes and vitreous carbon electrodes have been found to be inefficient for routine production of large nuclide quantities and the ion-exchanger method has been preferred for this purpose.

SUMMARY OF THE INVENTION

By contrast, starting from the use of electrofixing mentioned at the outset, it has been found that an especially effective radionuclide separation from target material in a practically loss-free recovery of the latter and surprisingly higher yield of radionuclide is obtainable in a reduced time period by a process characterized in that it is carried out in a flow cell with a permanent electrode arrangement and the separation of the target liquid is effected while maintaining the fixing voltage. Further features of the invention are given in the patent claims and the following description.

The technique of the invention allows a smooth coupling of the radionuclide/target liquid separation to the radiotracer synthesis process with especially good economies by minimizing target losses with high nuclide yields and rapid processing especially matched to an automatic operation. This technique was developed starting from a cyclotron irradiated $H_2^{18}O$ target and thus will be described in the following substantially with reference to this specific example.

The process of the invention is based upon the following principle: polarizable or ionogenic carrier-free radionuclides, dissolved in liquids of low electrical conductivity are isolated from the solution in such manner that in an electric field the respective radio isotope in polarized or ionic form migrates to the oppositely charged electrode and there is fixed by a kind of "electroadsorption." It has been found that a coaxial geometry with a relatively large fixing electrode and the avoidance of field peaks is especially advantageous for the carrier-free collection of the radionuclides from the target liquid free from ionogenic additives. After the fixing of the radionuclides on the electrode, the target liquid can be practically quantitatively removed from the radionuclides while the electric field is maintained. Upon a subsequent removal of the electric field or brief polarity reversal of the electrodes, the radioisotope anions or cations can again be brought into solution for which purpose especially high purity, "normal" water can serve. Then the on-line distribution of the aqueous active solution to the synthesis boxes can follow.

The flow cell of the invention can be connected especially directly in the transport path from the radiation station to the radiotracer synthesis (for example production of $^{18}F$-fluordesoxyglucose) or synthesis apparatus or can form optionally a part of the transport duct or the synthesis apparatus itself. Contemplated as electrode materials are materials which on the one hand exclude under the given conditions a chemical reaction or irreversible insertion of the radionuclides in the electrode material and, on the other hand, allow the radionuclide to go into solution upon polarity reversal of the system. Vitreous carbon (Sigradur®) and platinum fulfill these requirements. Before dissolution of the radionuclide from the electrode the latter can, while the field is applied, advantageously be subjected to "intermediate" rinsing, and the subsequent dissolution of the nuclide can be effected with cut-off of the field and optionally with heating. The solvent can be high purity water or optionally a solvent provided for the subsequent synthesis of the radiotracer (for example acetonitrile optionally with additions of dissolving agents, for example complex formers). The voltage source is preferably a direct current source which can yield voltages stepwise up to about 30 volts. For the deposition, field strengths are preferred which preferably do not exceed 100 V/cm. A "closed" surface of the fixing electrode which is as smooth as possible appears to be preferable.

BRIEF DESCRIPTION OF THE DRAWING

Further details of the invention are given in the following examples with reference to the accompanying drawings. They show in detail.

DETAILED DESCRIPTION OF THE DRAWINGS

Figure 1:
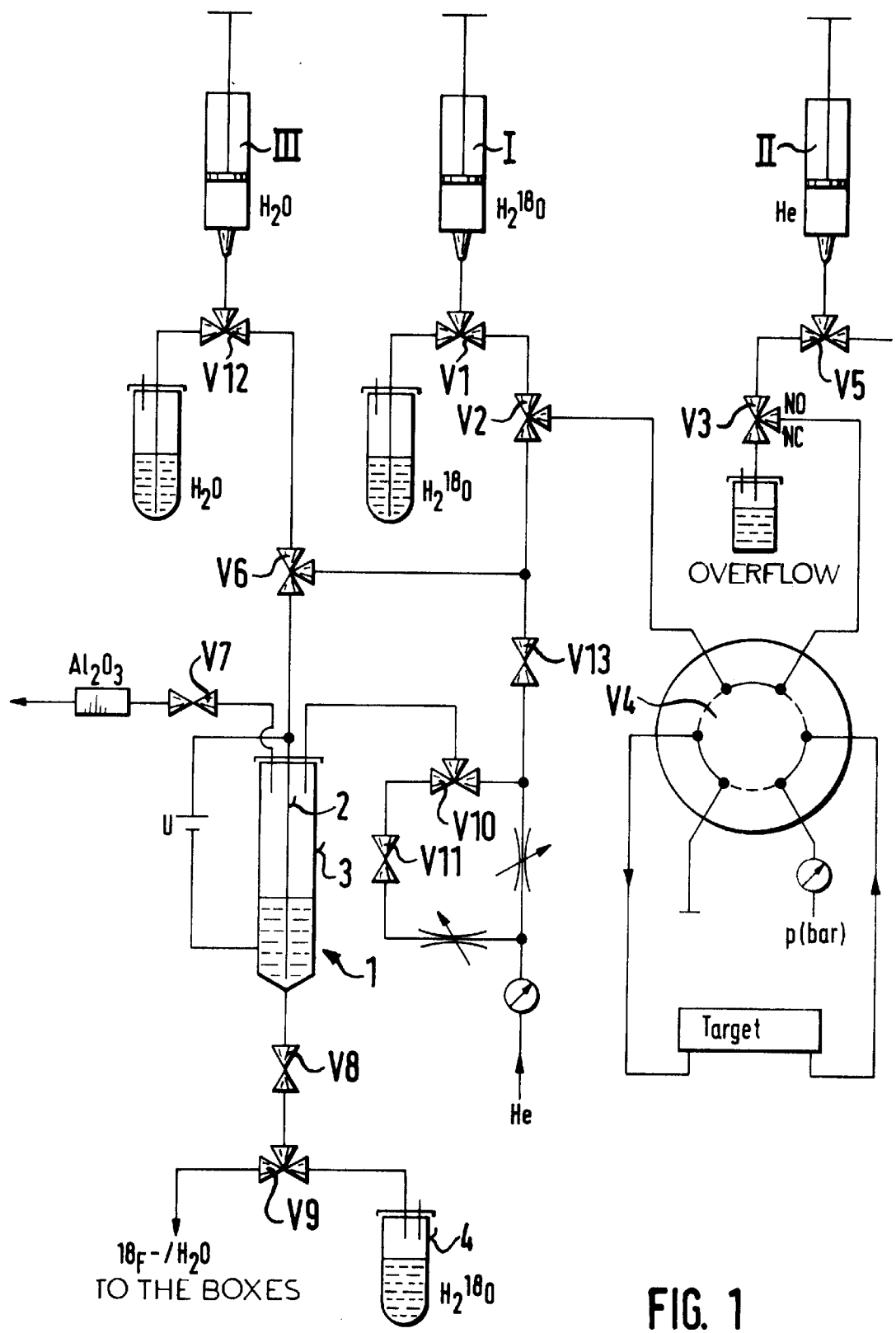
FIG. 1 a diagram of a separating apparatus with a flow cell.

According to FIG. 1, an arrangement for the separation of $^{18}F$ from cyclotron irradiated $H_2^{18}O$ encompasses a flow cell 1 with an electrode 2 formed as a supply capillary and a substantially cylindrical anode 3 forming a wall of the vessel. The diagram will be understandable without more from the process steps given in the following for radionuclide/target liquid separation:

1. Transport of the $^{18}F$ containing target liquid ($H_2^{18}O$) from the irradiation station (target) to the flow cell.

By means of the gas-filled (helium) syringe II, the aqueous phases from the target is displaced through the valves V2 and V6 into the flow cell 1. The controlled slow transport prevents a spraying of the $^{18}O$ water fed through the capillary 2 to the cell within the cell at the lower end.

2. Deposition of $^{18}F$ by electroadsorption.

With a direct current voltage of 20 V the negatively charged fluoride ions are deposited and fixed on the Sigradur® shell 3 which is anodic by comparison with the cathodic capillary 2, within about 6 minutes. After the electroadsorption of the $^{18}F$, the $^{18}O$ water free from the iogenic additives is transported, while the electrical field is maintained, with a weak controllable helium stream which is fed via the valves V11 and V10, into the collecting vessel 4. The water used for the radiation is thus substantially quantitatively recovered.

3. Transfer of the electrofixed $^{18}F$ into "normal" water.

Two milliliters of water are filled into the cell 1 by means of the syringe III via the valves V6 and V12. For rapid and quantitative transfer of the $^{18}F$ into the aqueous phase, the water during reversal of polarity of the electric field (the platinum capillary 2 becomes an anode) is preferably warmed. For this purpose, the Sigradur® shell 3 is brought to a temperature of about 50° C. by a resistance heater.—For the dissolution process the field maintained during the removal of the $H_2^{18}O$ from the cell and an optionally subsequent "intermediate rinsing" and applied for the fixing, can be reversed only briefly and then shut off or only shut off.—The $^{18}F$ containing water is transported after about 5 minutes with the aid of a helium current via valves V8 and V9 through a polypropylene tubing to the synthesis modules (boxes).

4. Drying of the cell for preparation of the system for a new separation.

The empty cell 1 is—with simultaneous heating of the Sigradur® shell 3—dried by a helium current so that a new filling of the cell with $^{18}F/^{18}O$ water will not result in a dilution of the target water and consequently a reduction in quality thereof. In the drying process helium is supplied via the valves V13 and V6 through the platinum capillary and is conducted for the valve V7 and the $Al_2O_3$ cartridge coupled therewith to the exterior. The cartridge has the function of filtering possible gaseous $^{18}F$ and thus avoids a contamination of the environment. The drying lasts about 15 minutes. (The valve V7 is open during each filling step and during the electroadsorption and desorption).

The steps 1 to 3 occupy in total about 15 minutes.

Figure 2:
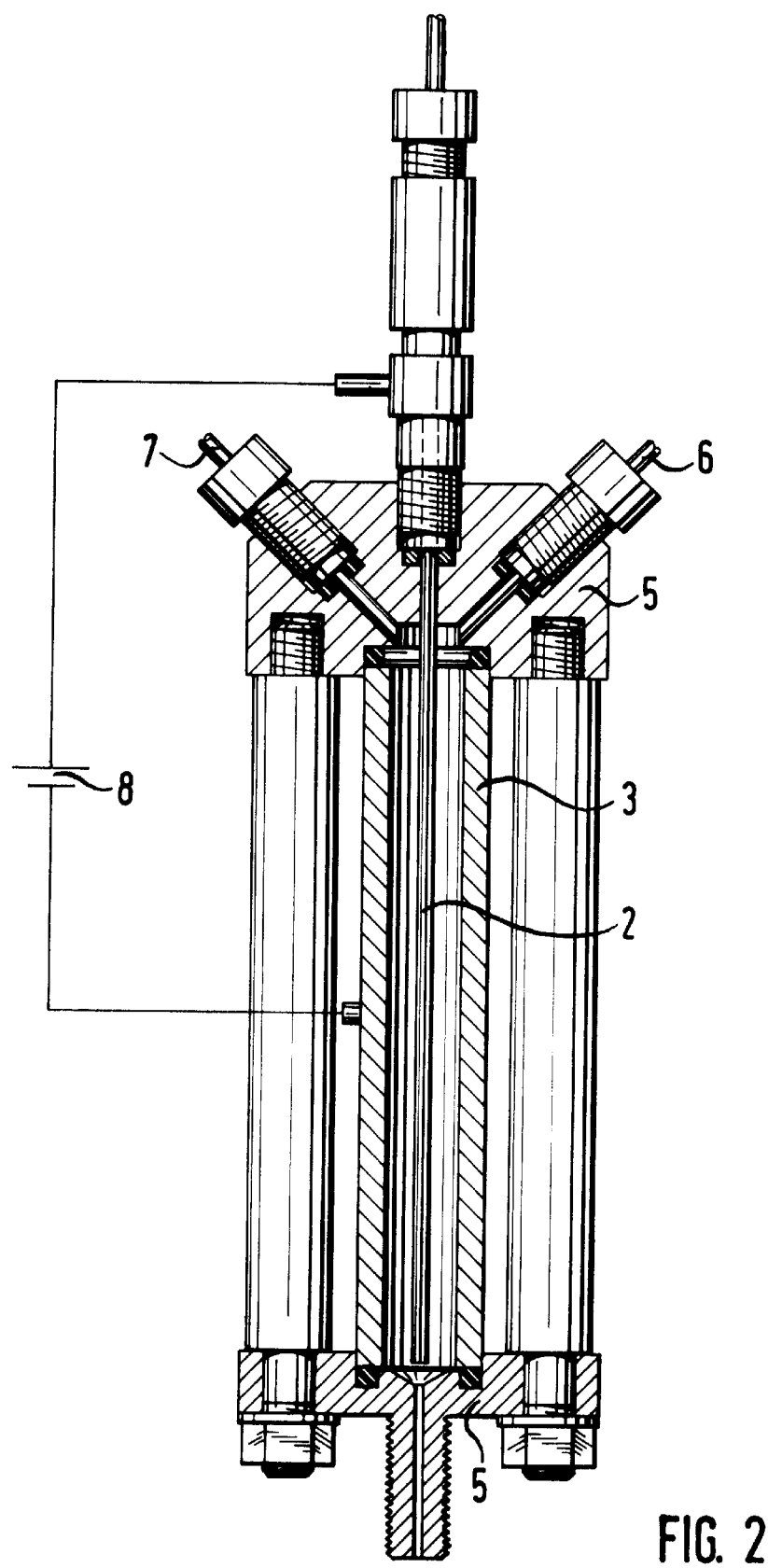
FIG. 2 a flow cell suitable therefor in detail.

According to FIG. 2 the flow cell is comprised substantially of the shell 3 and an axial platinum capillary 2 through which the cylindrical vessel is filled or the inert gas is introduced into the chamber. The height of the cylinder is so dimensioned that the level of the $^{18}F/H_2^{18}O$ solution occupies about 50 to 70% of the total volume. The internal volume of the platinum capillary amounts to 35 $\mu l$. In a normal filling state the liquid volume within the capillary is about 20 $\mu l$ so that the liquid quantity remaining therein only amounts to 1–2% of the total volume involved in the $^{18}F$ fluoride deposition. The system is fixed and sealed by a plastic holder 5. At the lower end of the holder, a flat funnel is machined into which opens the water discharge duct. In the head part of the holder 5, made from PEEK, there is found a helium supply line V6 as well as an opening 7 through which the gas can be conducted to the exterior. A controllable gas current enables a controlled emptying of the cell. The Sigradur® cylinder 3 and the platinum capillary are connected to a direct current source 8 and can be selectively switched as cathode or anode. In addition, the flow cell can be heated by a hot air stream or an electrical heater, for example a heating coil. It is especially advantageous to complete the apparatus with a program controller which serves for the voltage energization and heating of the cell.

In the illustrated example, the Sigradur® cylinder has a length of 70 mm and an internal diameter of 7 mm. The internal diameter of the platinum capillary amounts to 0.8 mm and the electrode spacing to 2.7 mm.

These numerical values are only examples which, as is self understood, can be varied according to the respective practical requirements, in which case consideration should be given to the fact that the target liquid in a batch operation of the cell should be preferably supplied with a certain buffer volume left free and an electrode spacing which will have rapid transport of the ions to the electrode to minimize activity losses as isotopes with short half lives.

Figure 3A:
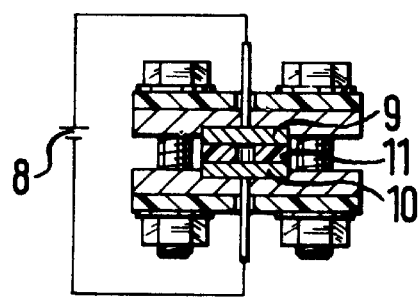
FIG. 3 a diagram of a flow cell acting as a part of a duct.
Figure 3B:
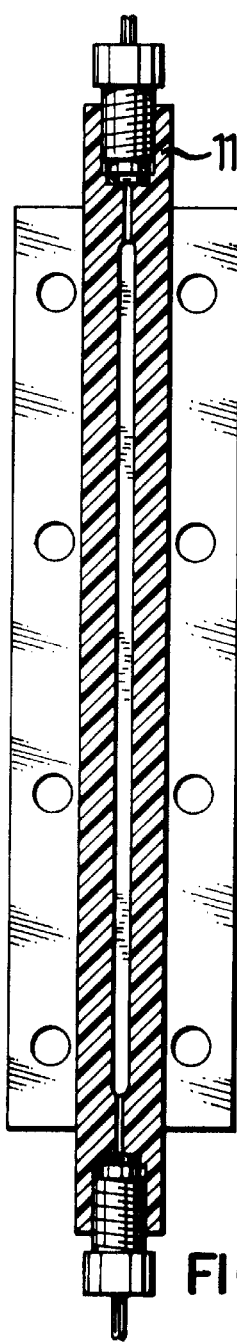
Figure 3C:
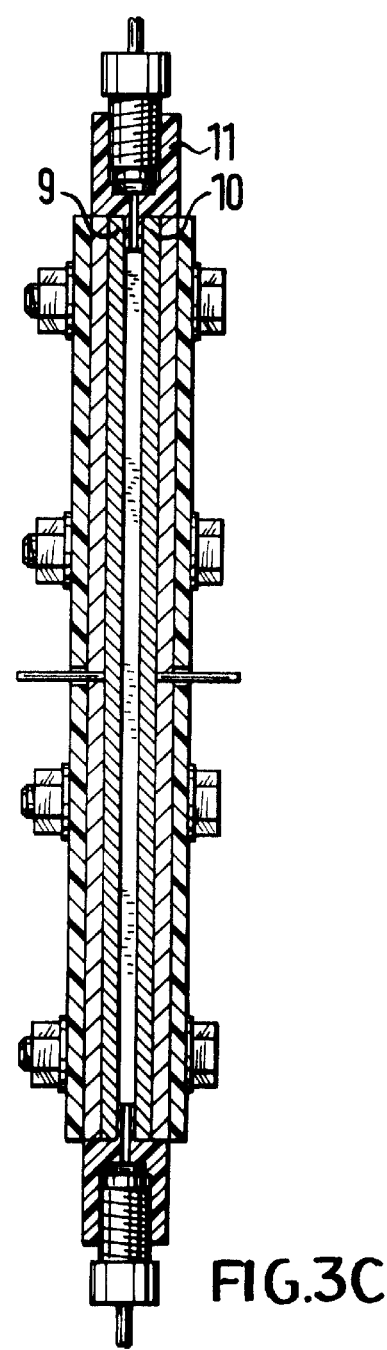

An alternative flow cell for the $^{18}F/H_2^{18}O$ separation is illustrated in FIG. 3. It encompasses two parallel Sigradur® plates 9, 10 which have a spacing of about 2 mm. Corresponding to FIG. 3 the plates functioning as electrodes are separated from one another by a peripheral extending plastic strip 11 which serve both for an electrical isolation and also has a seal for the centrally-arranged rectangular passage through which the $^{18}F$ solution can be continuously conducted while the field is applied.

After the electrofixing of the $^{18}F$ fluoride, the cell can be rinsed with an organic solvent and thus freed from residual water. After polarity reversal, the fluoride can be transferred nonaqueously into the organic solvent in the presence of a solution of a phase transfer catalyst and thus exists, without thermal dewatering, available for a nucleophilic synthesis of $^{18}F$ radiopharmaceuticals as has been described, for example, in EP 0 167 103 B1.

Figure 4:
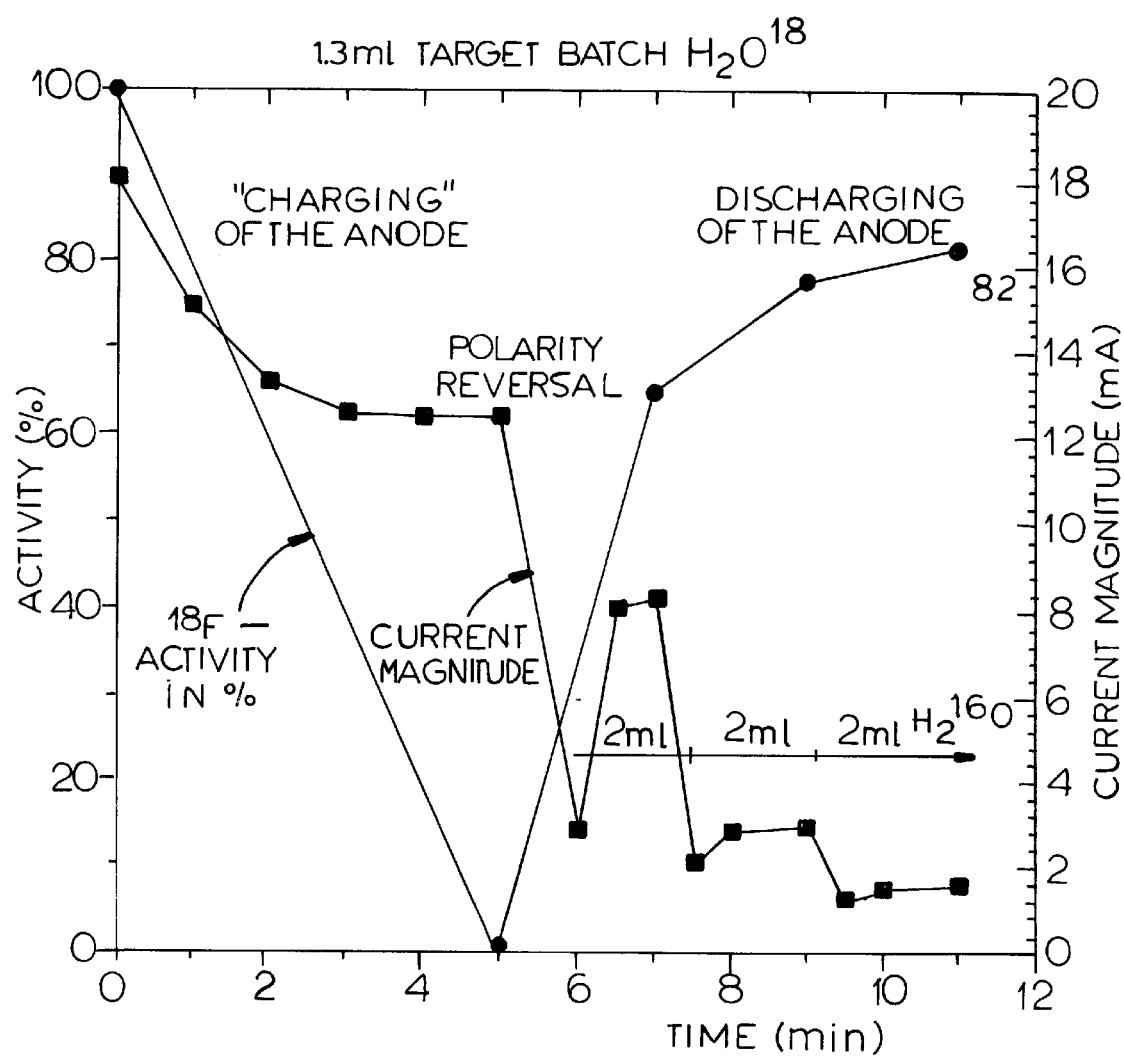
FIG. 4 a graph of an example of the electrofixing and electroresolubilization of a radionuclide.

The diagram of FIG. 4 shows by way of example, the results of the separation of $^{18}F$ fluoride from $H_2^{18}O$. At a voltage of 20V, $^{18}$F is quantitatively fixed on the Sigradur® anode. In the course of the deposition, a time-dependent current reduction is distinguishable which reaches standstill after about 5 minutes. The desorption of the radionuclide upon polarity reversal of the field in the presence of normal water is measured time-dependently the activity yield of 82% obtained in this case after three times water replacement (each 2 ml) does not correspond to the practically obtainable results. A one time water supply and opposite polarization with simultaneous heating of the flow cell gives rise to a $^{18}$F recovery of about 90%.

We claim:

1. A process for separating a carrier-free radionuclide from a liquid or liquefiable target material containing a radionuclide and having reduced electrical conductivity which results from a nuclear process, in ionizable or polarizable form, which comprises the steps of:

(a) providing a permanent electrode arrangement in a flow cell which comprises:
   (1) a vitreous carbon cylinder as an outer
   (2) a counter electrode in the form of a platinum capillary within said vitreous carbon cylinder and extending over an entire length of the cylinder which terminates via a flat cone in a capillary spaced from a valve and at its upper end in a cap closing the cylinder and holding the counterelectrode with an inert gas-connecting fitting and a pressure equalization opening;

(b) feeding the liquid or liquefiable target material containing the radionuclide to the flow cell through the platinum capillary in the counterelectrode;

(c) applying an electrical field to the liquid or liquefiable target material for electrofixing the radionuclide on one of the electrodes;

(d) following step (c), separating the liquid or liquefied target material from the radionuclide by removing the liquid or liquefied target material from the flow cell while maintaining a fixing voltage in said flow cell; and (e) forming a solution of the carrier-free radionuclide separated according to step (d) with a shut-off field or in a field of opposite poling.

2. The process according to claim 1 characterized in that according to step (a) an electrode arrangement is chosen with pore-free inert surfaces.

3. The process according to claim 2 characterized in that one chooses as the electrode for the electrofixing of the radionuclide the wall of the vessel.

4. The process according to claim 3 characterized in that according to step (c) the electrofixing of the radionuclide is effected in a coaxial field with enrichment of the radionuclide on the cylindrical outer electrode.

5. The process according to claim 4 characterized in that according to step (b) the liquid feed to the cell is effected via the axial electrode which is formed as a capillary.

6. The process according to claim 1 characterized in that according to step (c) the electrofixing of the radionuclide is effected at field strengths of 10 to 100 V/cm.

7. The process according to claim 1 characterized in that it is carried out according to step (c) with a fixing electrode surface area of at least 3 cm$^2$.

8. The process according to claim 1 characterized in that the solubilization of the nuclide from the electrode according to step (e) is effected with heating.

9. The process according to claim 1 characterized in that according to step (d) the liquid or liquefied target material is removed from the flow cell by an inert gas.

10. The process defined in claim 1 which further comprises the step of:

(f) distributing on line the solution containing the carrier-free radionuclide formed in step (e) for organic synthesis.

11. A method for marking an organic compound with a radioisotope which comprises the step of subjecting the organic compound to nucleophilic exchange with the solution of the carrier-free radionuclide distributed according to claim 10.

* * * * *